United States Patent [19]

Januszewski et al.

[11] 4,159,316

[45] Jun. 26, 1979

[54] SELF-HEATING DENTIFRICE

[75] Inventors: Joseph P. Januszewski, Somerville; Lesley J. Altan, Somerset, both of N.J.

[73] Assignee: Colgate Palmolive Company, New York, N.Y.

[21] Appl. No.: 884,292

[22] Filed: Mar. 6, 1978

[51] Int. Cl.² ............................................. A61K 7/16
[52] U.S. Cl. .................................................... 424/49
[58] Field of Search .................................... 424/49–58

Primary Examiner—Shep K. Rose
Attorney, Agent, or Firm—Robert L. Stone; Murray M. Grill; Herbert S. Sylvester

[57] ABSTRACT

There is disclosed a stable anhydrous self-heating dentifrice which contains an anhydrous synthetic zeolite as the sole or major abrasive, a hydroxypropyl cellulose gelling agent and a propylene glycol humectant as the essential ingredients.

10 Claims, No Drawings

SELF-HEATING DENTIFRICE

This invention relates to a novel anhydrous self-contained heating dentifrice capable of generating heat in the oral cavity, immediately upon contact therewith, as when brushing one's teeth, and containing zeolite as the sole or major polishing agent, hydroxypropyl cellulose gelling agent, propylene glycol humectant and a suitable flavor; and to the method of making said dentifrice.

PRIOR ART

The prior art discloses self-heating cosmetic preparations as shown in U.S. Pat. No. 3,341,418 to Moses et al. Said patent discloses a two-part aqueous liquid composition, to be applied to the skin as a shaving cream, or to the hair as a shampoo, packaged in a dual compartment container and to be simultaneously dispensed for exothermic reaction with each other, one compartment containing an oxidant such as hydrogen peroxide or the like in an aqueous medium and the other compartment containing a reducing agent such as thiourea and the like in an aqueous medium.

U.S. Pat. No. 3,250,680 to Menkart et al also discloses a heat-generating cosmetic composition adapted to evolve heat when it contacts moisture which is an anhydrous composition containing about 5 to 40% of an anhydrous adsorbent material such as alkali metal alumino-silicate molecular sieves dispersed in a non-aqueous cosmetically-acceptable vehicle such as mineral oil or liquid polyalkylene glycol. The cosmetic compositions disclosed herein include skin and hand creams, shampoos and toothpaste. However, the toothpaste formula therein does not contain the propylene glycol humectant, the hydroxypropyl cellulose gelling agent, and flavoring agents, nor is the sodium aluminum silicate the sole or major polishing agent. As a matter of fact, its content is less than that of each of the other two polishing agents. The presence of the propylene glycol-hydroxypropyl cellulose vehicle in the form of a gel is essential in present novel dentifrice to effect a stable, anhydrous, self-heating dentifrice.

DESCRIPTION OF THE INVENTION

It has been found that it is necessary to use a hydroxypropyl cellulose as the gelling agent with the propylene glycol humectant in the production of an anhydrous system or base for anhydrous zeolites in order to produce a stable, self-heating dentifrice, said heat being self-contained and releasable when the dentifrice is used in the normal manner, and not prior thereto (i.e. while in the tube or aerosol container or during its manufacture). Other gums such as sodium carboxymethyl cellulose, hydroxyethyl cellulose, polyvinyl alcohol, Irish Moss, silica aerogel and the like cannot be used since these gums require water to gel, and water would be detrimental to the anhydrous dentifrice. Other known dentifrice humectants such as glycerin, and oils such as mineral and vegetable oils cannot be used due to incompatibility and/or their water content. Even a water content of only 2% causes the dentifrice to swell up the tubes within 1-2 days at elevated temperatures and within 1-2 weeks at room temperature. This swelling may be attributed to trapped gases in the zeolite which are eventually released by heat and/or are displaced by one or more of the ingredients in the formulations (i.e. flavor + propylene glycol) or moisture pick up during the formulation process.

Similarly, a formulation containing about 52% glycerine, 3% of a polyethylene glycol (molecular weight about 600) binder, and 29% zeolite also exhibited swelling in the dental tubes and the resultant dental cream became thin and airy or feathery in appearance due to the entrapped gas, even after deaerating the formulation.

Thus, it is apparent that it is essential to use specific anhydrous ingredients such as the humectant propylene glycol, and gelling agent hydroxypropyl cellulose in order to eliminate swelling in the tubes and enhance the stability of the formulation in the tube or other containers (i.e. increase its shelf-life), as well as to maintain the proper consistency of the dental cream during its useful life. The consistency of the dental cream must be such that it does not flatten out, become stiff, thick or lumpy upon standing; but retains its original non-dripping soft form.

It has been unexpectedly found that the inherent problems in an anhydrous dental cream have been overcome by utilizing a specific humectant and gelling agent (i.e. propylene glycol gelled with hydroxypropyl cellulose) as the vehicle base for the zeolite abrasive in the production of self-heating dentifrices.

Accordingly, it is an object of this invention to provide a stable anhydrous dentifrice with a self-contained heating effect, capable of being extruded from a tube or other containers, containing the specific vehicle base, the propylene glycol-hydroxypropyl cellulose gel.

Another object of this invention is to provide an anhydrous self-heating dentifrice possessing a thermal effect in the oral cavity.

Accordingly, the present invention relates to a stable anhydrous self-heating dentifrice consisting of a finely divided anhydrous synthetic zeolite having an appreciable heat of hydration and capable of being reversibly dehydrated as the sole or major polishing agent in amounts of about 20 to 50% by weight, about 0.1 to 5% by weight of at least one flavoring agent, and about 20 to 75% of an anhydrous liquid vehicle consisting essentially of propylene glycol gelled with hydroxypropyl cellulose.

The synthetic zeolites which are the source of heat and abrasivity in the present self-heating formulations are crystalline metal alumino silicates wherein the metal may be an alkali metal, an alkaline earth metal, zinc, copper or a mixture of metals and having an appreciable heat of hydration, and capable of being dehydrated and at least partially rehydrated without destroying the framework structure of the zeolite.

Zeolite has been defined by Smith, J. V., Mineralogical Society of America, Special Paper No. 1, 1963, as an aluminosilicate with a framework structure enclosing cavities occupied by large ions and water molecules, both of which have considerable freedom of movement permitting ion exchange and reversible dehydration.

A synthetic zeolite useful in this invention is typically commercially available from the Linde Division of Union Carbide Corporation, New York, N.Y. as molecular sieves. These materials are fully described in U.S. Pat. Nos. 2,882,243 and 2,882,244. The structure of the A and X crystals may be represented as follows:

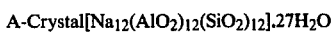

A-Crystal[$Na_{12}(AlO_2)_{12}(SiO_2)_{12}$].$27H_2O$

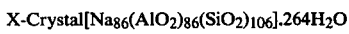

X-Crystal[$Na_{86}(AlO_2)_{86}(SiO_2)_{106}$].$264H_2O$

On heating, the water is removed leaving the crystal structure intact with an aluminum-oxygen-silicon structure.

The AlO$_2$ has one negative charge available for cation exchange. By making use of this property, the "pore size" can be varied.

The crystal symmetry of A-zeolites are cubic and the unit cell dimension is about 12.5 Å on each side. In the A-crystal the pores range from 3 to 5 Å and with the X-crystal from 8 to 12 Å. The X-crystal also has a cubic symmetry.

Molecules, if not too large, pass through the pores and are adsorbed on the inner surface and held by electrostatic forces. As materials are adsorbed in the sieves, more or less heat is evolved and in some cases where this energy is high, it causes the sieves to glow. The sieves rapidly take up the maximum amount of material (cavities full) and the partial pressure over the loaded sieve in some cases is very low.

The A-crystal with the small pore size is best suited for holding water and hence adapted to techniques and procedures where drying is the primary objective. The X-crystal with the larger pore size is usually preferred for loading since there is less limitation of the molecular size which can pass through the pore. Pore size affects the rate of displacement of adsorbed material but not the equilibrium.

The ability of the pores to pass certain molecules and exclude others has been the basis for a number of the present applications for separating similar compounds. For example, normal hydrocarbons readily pass through the pores whereas isohydrocarbons do not.

Materials adsorbed on the sieves may be released by heating, reduced pressure or by displacement by a more strongly adsorbed compound. For instance, water will remove any adsorbed material. The higher the molecular weight, the slower is the displacement by any means. Metal ions such as copper, zinc, alkali metals, magnesium, calcium, and other alkaline earth metals are taken up or replaced in these sieves in accordance with the selectivity and capacity of each of these ions. However, the zeolites containing any of the aforementioned metal ions are equally effective in conjointly releasing heat and the adsorbed flavor components upon contact with water.

Commercially available synthetic zeolites are suitable for use as the sole or major dental polishing agent in instant dentifrice formulations, and possess acceptable abrasivity for effective cleaning and polishing of the teeth, with the added advantage of releasing appreciable heat of hydration within the oral cavity substantially instantaneously so as to afford a pleasurable warm sensation coupled with an immediate flavor release. The thermal effects are illustrated by the following tests, wherein water is added to zeolite 4A to determine the heat release of the zeolite.

TABLE I

| Zeolite (gms) | Water added (gms) | Initial temp. of H$_2$O (°C.) | Recorded temp. (°C.) | Time |
|---|---|---|---|---|
| 2 | 4 | 25 | 50 | seconds |
| 2 | 3 | 25 | 58 | seconds |
| 2 | 2.5 | 25 | 62 | seconds |
| 2 | 2.0 | 25 | 64 | seconds |
| 2 | 3.0 | 25 | 55 | seconds |
| 2 | 3.0 | 27 | 62 | seconds |
| 1 | .5 | 25 | 66 | 30 seconds |
| 1 | 1 | 25 | 55–60 | 30 seconds |
| 1 | 1.5 | 25 | 45 | 30 seconds |
| 5 | 2.5 | 25 | 100–120 | seconds |

TABLE I-continued

| Zeolite (gms) | Water added (gms) | Initial temp. of H$_2$O (°C.) | Recorded temp. (°C.) | Time |
|---|---|---|---|---|
| 5 | 7.5 slurry[1] | 25 | 26–30 | seconds |
| 7.5 slurry[1] | 2.5 | 30 | 68 | 30 seconds |
| 5 slurry[1] | 2.5 | 25 | 50 | 15 seconds |
| 9.1 slurry[2] | 2.0 | 25 | 70 | seconds |

[1]slurry contains 48.387% zeolite 4A and 51.613% propylene glycol.
[2]slurry contains 4.1 gms zeolite powder and 5.0 gms propylene glycol.

This table clearly shows that there is an appreciable release of heat upon the addition of small amounts of water to the zeolite or to a propylene glycol slurry of zeolite, said heat release occurring within seconds after water contact.

Zeolites particularly useful herein include the molecular sieves named zeolite A which has the following properties:

A chemical composition defined heretofore, a cubic crystalline symmetry, the cell dimension being equal to 12.32 Å (calculated for dehydrated zeolite), a density of 1.33 g/cc (calculated for dehydrated zeolite), a void volume of 0.3 cc/g (based on the amount of water contained per gram of dehydrated zeolite), and an aperture size of 4.2 Å;

Zeolite X which has the following properties: a chemical composition previously defined herein, a cubic crystalline symmetry, a cell dimension of 24.95 Å (dehydrated zeolite), a density of 1.29 g/cc (dehydrated zeolite, a void volume of 0.36 cc/g, and an aperture size of 8 Å;

Zeolite Y of the following chemical composition:

$$Na_{56}[(AlO_2)_{56}(SiO_2)_{136}] \cdot 264H_2O$$

which has a cubic symmetry and a cell dimension of 24.7 Å, a density of 1.30 g/cc (dehydrated), a void volume of 0.35 cc/g, and an aperture size of 8 Å;

Zeolite B of the following chemical composition:

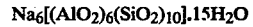

$$Na_6[(AlO_2)_6(SiO_2)_{10}] \cdot 15H_2O$$

which is cubic in symmetry and has a cell dimension of 10.0 Å, a density of 1.47 g/cc (dehydrated), a void volume of 0.15 cc/g, and an aperture size of 3.5 Å;

Synthetic mordenite of the following chemical composition:

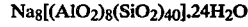

$$Na_8[(AlO_2)_8(SiO_2)_{40}] \cdot 24H_2O$$

which is orthorhombic in symmetry, has a density of 1.72 g/cc (dehydrated), has a void volume of 0.14 cc/g and an aperture size of 6.6 Å.

The above described zeolites may be varied by exchanging all or part of the sodium ions with other cations such as hydrogen and/or metal ions including the alkali metals, alkaline earth metals, zinc or copper or mixtures thereof.

The uniformity in composition and physical properties of the synthetic zeolites renders it particularly useful herein as opposed to natural occurring zeolites wherein the physical properties are non-uniform.

The synthetic zeolites can readily be dehydrated to remove substantially all the water by heating it in air or vacuum to temperatures up to 600° C., and preferably to a temperature of about 350° C. in a vacuum of 10$^{-5}$ mmHg, without destroying the crystal structure thereof. Stability to heat has been observed up to temperatures of about 700° C. The proportion of anhydrous synthetic zeolite in the dentifrice may be from about 20 to 50% by weight and preferably about 30 to 45%.

The anhydrous synthetic zeolite has the property of generating heat of hydration when water is added thereto as illustrated by Table I. Accordingly, the presence of said anhydrous zeolite in an anhydrous liquid vehicle imparts a thermal effect in the oral cavity.

The substantially anhydrous vehicle of this invention is preferably formulated from the following: (1) propylene glycol humectant; (2) hydroxypropyl cellulose gelling agent; (3) standard toothpaste additives; and optionally, (4) water incompatible dentifrice additives, additional abrasives and inert ingredients.

The above-mentioned ingredients must, of course, be non-toxic and substantially anhydrous.

The dentifrice formulation of this invention includes liquids and solids that are proportioned as further defined hereinafter to form a creamy mass of desired consistency which is extrudable from a pressurized container or a collapsible tube (for example aluminum). In general, the liquids in the dental cream will comprise chiefly propylene glycol, in an amount of at least 35% by weight and preferably about 35 to 60%. It is essential to use the hydroxypropyl cellulose as the gelling agent in instant dental creams. The solid portion of the vehicle is usually present in an amount of up to about 10 percent and preferably about 0.2 to 5 percent by weight of the formulation.

The propylene glycol (1,2-Propanediol) which constitutes the major ingredient in present dentifrice is a clear, colorless, odorless, viscous liquid completely miscible with water, having a specific gravity of 1.035–1.039 and a boiling point of 184° C.–189° C., and is anhydrous (i.e. preferably contains a maximum of 0.2% water). Since propylene glycol absorbs moisture when exposed to moist air, it must be preserved in air-tight containers. Accordingly, the process of compounding this formulation should be conducted in a substantially anhydrous environment such as in a low humidity room or preferably under vacuum of at least about 20 inches mercury and preferably 28–30 inches.

A particular advantage of using the propylene glycol humectant in instant anhydrous self-heating dentifrice resides in the fact that no heat is produced when this humectant is added to the zeolite, whereas heat is evolved with other humectants as evidenced by the rise in temperature from room temperature (22° C.), when using humectant and the zeolite 4A in the approximate ratio of humectant to zeolite normally found in anhydrous dentifrices.

TABLE 2

| Humectant | Humectant:Zeolite | Temp. °C. |
| --- | --- | --- |
| propylene glycol | 1:1.3 | 22[1] |
| glycerin | 1:1.3 | 29–30 |
| sorbitol | 1:1.3 | 34–35 |
| water | 1:1.3 | 55 in seconds |

TABLE 2-continued

| Humectant | Humectant:Zeolite | Temp. °C. |
| --- | --- | --- |
| | | dropped to 38° C. |

[1]Heat is only produced upon the addition of water to the propylene glycol and zeolite combination.

Thus, it is apparent that the compounding of the formulation is simplified and there is no heat loss prior to its use in the oral cavity. This unique feature permits the pretreatment of the zeolite with the propylene glycol if and when desired in order to release some or all of the trapped gases and/or to plug up the crevices in the abrasive with the propylene glycol. This is additionally effective in reducing the swelling in the tubes, thereby further increasing the shelf-life and stability of the dentifrice.

Another essential ingredient in the present anhydrous dentifrice is hydroxypropyl cellulose gelling agent, which is a physiologically inert, cellulosic polymer having a molecular weight of 60,000–1,000,000 in the form of an off-white, odorless, tasteless, granular solid.

A hydroxypropyl cellulose useful in this invention is typically commercially available from Hercules Co. as Klucel, which is in the form of a fine powder having a particle size such that 95% passes through a 30 mesh sieve and 99% passes a 20 mesh sieve, with a moisture content that does not exceed 5% by weight and is generally between 2 and 3%.

The FDA defines the food additive hydroxypropyl cellulose as a cellulose ether containing propylene glycol groups attached by an ether linkage and containing on an anhydrous basis, not more than 4.6 hydroxypropyl groups per anhydroglucose unit. This additive has a minimum viscosity of 145 centipoises for a 10% by weight aqueous solution at 25° C.

Klucel is manufactured by reacting alkali cellulose with propylene oxide at elevated temperatures and pressures. The propylene oxide can be substituted on the cellulose through an ether linkage at the three reactive hydroxyls present on each anhydroglucose monomer unit of the cellulose chain. Published information suggested that the etherification takes place in such a way that the hydroxypropyl substituent groups contain almost entirely secondary hydroxyls. The secondary hydroxyl present in the side chain is available for further reaction with the oxide, and chaining-out may take place. This results in the formation of side chains containing more than one mole of combined propylene oxide.

Data from studies with Klucel suggest that all of the primary hydroxyls on the cellulose have been substituted and that the only reactive groups remaining are secondary hydroxyls. Some typical molecular weight values ($M_w$) are: H-type 1,000,000; G-type 300,000; L-type 100,000; E-type 60,000.

An idealized structure for a portion of a hydroxypropyl cellulose molecule with a molar substitution (M.S.) of 3.0 is given.

IDEALIZED STRUCTURE OF HYDROXYPROPYL CELLULOSE (M.S. 3.0)

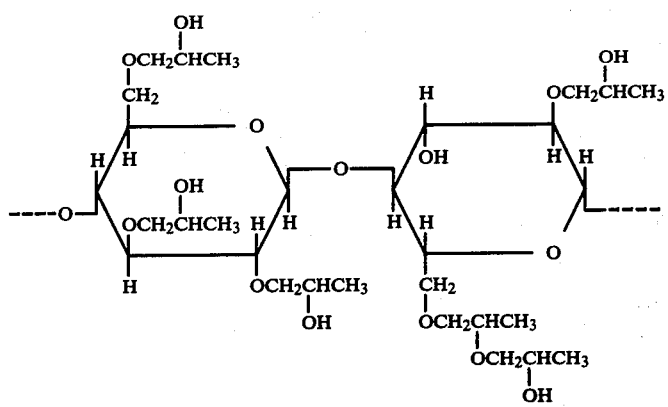

Klucel is available in a wide range of viscosities, depending on the molecular weight, with the G-Type being intermediate in viscosity between the high (H) and very low (E) viscosity types. The lower viscosity types are more readily soluble in water below 40° C. and in a wide range of organic solvents (i.e. methyl and ethyl alcohol, propylene glycol, dioxane, etc.), than the high viscosity types. At elevated temperatures, Klucel is insoluble in water, but soluble in organic solvents. The viscosity of an aqueous Klucel solution decreases as the temperature increases up to 40° C. at which temperature the Klucel starts to precipitate out. The viscosity of solutions of Klucel in organic solvents similarly decreases at elevated temperatures, but does not precipitate out at temperatures above 40° C. The viscosity of Klucel solutions, both aqueous and organic, increases rapidly with concentration and is also a function of the molecular weight of the type polymer. For example, the viscosity of 1% H polymer in water is 1,900 cps and in propylene glycol is 8,590 cps; 2% G polymer in water is 270 cps and in propylene glycol is 6,640 cps; 5% L polymer in water is 80 cps and in propylene glycol is 5,020 cps; 10% E polymer in water is 275 cps and in propylene glycol is greater than 10,000 cps. These viscosities are only typical values and some variation will be obtained from lot to lot of each Klucel type. All viscosities are determined at 25° C. using a Brookfield LVF viscometer (4 spindles and 4 speeds covering the range 0 to 100,000 cps). The following table records the viscosities of the various types of Klucel at varying concentrations.

TABLE 3

| Types | | Concentration in water by weight | | | |
|---|---|---|---|---|---|
| Standard | Food | 1% | 2% | 5% | 10% |
| H | HF | 1500-2500 | | | |
| HW | HWF | 1500-2500 | | | |
| M | MF | | 4000-6500 | | |
| G | GF | | 150-400 | | |
| J | JF | | | 150-400 | |
| L | LF | | | 75-150 | |
| E | EF | | | | 200-300 |
| Types | | Concentration in Anhydrous Ethanol By Wt. | | | |
| Standard | Food | 1% | 2% | 5% | 10% |
| H | HF | 1000-2500 | | | |
| HW | HWF | (no specification) | | | |
| M | MF | | 3000-6500 | | |
| G | GF | | 75-400 | | |

TABLE 3-continued

| | | |
|---|---|---|
| J | JF | 75-400 |
| L | LF | 25-150 |
| E | EF | 100-300 |

The proportion of the gelling agent hydroxypropyl cellulose in the present dentifrices is sufficient to form an extrudable, shape-retaining product which can be squeezed from a tube onto a toothbrush and will not fall between the bristles of the brush but rather, will substantially maintain its shape thereon. In almost all cases no more than about 5% of gelling agent need be used and preferably about 1 to 5%.

The liquid vehicle of the dentifrice, together with the gelling agent and other constituents, forms an extrudable mass of a non-dripping consistency when extruded from a collapsible tube, such as an aluminum tube. Thus, by the addition of more vehicle, the dental cream can be thinned and conversely, by the addition of more solids, especially more gelling agent, the products can be thickened. Normally the proportion of vehicle is determined by the physical properties of the extrudate. Usually, however, from about 10 to 90% of the vehicle will be employed, with about 10 to 35% being a typical range for the production of dentifrices.

Any suitable flavoring or sweetening sialagogues or mixture thereof may be employed in formulating a flavor for the compositions of the present invention. Examples of suitable flavoring constituents include the flavoring oils, e.g. oils of spearmint, peppermint, wintergreen, sassafras, clove, sage, eucalyptus, marjoram, cinnamon, lemon, lime, grapefruit and orange, as well as flavoring aldehydes, esters such as methyl salicylate, alcohols, and higher fatty compounds known in the art. Also useful are such chemicals as menthol, carvone and anethole. Of these, the most commonly employed are the oils of peppermint, spearmint, and eucalyptus and anethole, menthol and carvone. In some cases flavorful solvents, such as chloroform and mock chloroform, may be employed. Such flavorings may be used as liquids or may be solidified by being mixed with a particulate carrier material, such as starch, calcium carbonate, paraffin, vegetable wax, fat, higher fatty acid or other suitable carrier substances. In the cases of solid flavors, such as vanillin, sage, citric acid or licorice, the flavor may be converted to liquid form, if so desired, by dissolving it in the solvent or emulsifying it, usually with the help of a synthetic or natural emulsifying agent. The choice as to whether to utilize particulate solid or liquid flavors or to convert such flavors to a particulate solid or liquid form, respectively, will often depend on the properties desired in the flavor and its compatibility with the sweetener and any other material to be present with it. Suitable sweetening agents include mannitol, sucrose, lactose, maltose, sorbitol, xylitol, sodium cyclamate, saccharin, the dipeptides of U.S. Pat. No. 3,939,261 and the oxathiazin salts of U.S. Pat. No. 3,932,606. Suitably, flavor and sweetening agent may together comprise from about 0.1 to 10% or more of the compositions of the instant invention.

In the preparation of tooth powders, it is usually sufficient to admix mechanically, e.g., by milling, the various solid ingredients, in appropriate quantities and particle sizes and thereafter carrying out procedures known in the art for containerization of the product, preferably in a low humidity environment.

In chewable dental tablets the solids and liquids are proportioned similarly to the amounts in dental creams and the flavor is blended with the solids and liquids, and a waxy matrix such as polyethylene glycol having a molecular weight of about 6,000 by weight, generally in amounts of about 4–20 percent by weight, in order to facilitate the formation of a tablet of the desired size and shape.

The formulation of this invention may optionally include an additional dentally acceptable, substantially water insoluble anhydrous polishing agent of the type commonly employed in dental creams. The polishing agents are usually finely divided water insoluble powdered materials. Preferably, they are from 1 to 40 microns, most preferably from 2 to 20 microns in particle sizes, with distribution of particle sizes being normal over the range. Representative polishing agents include, for example, dicalcium phosphate, tricalcium phosphate, insoluble sodium metaphosphate, aluminum hydroxide, colloidal silica, magnesium carbonate, calcium carbonate, calcium pyrophosphate, bentonite, amorphous alkali metal or alkaline earth metal alumino-silicates having a refraction index of about 1.44–1.47 and containing at least 70% silica, up to about 10% alumina, up to about 10% sodium oxide and up to 10% moisture, etc., including suitable mixtures thereof. When employed, it is preferred to use a minor amount thereof, up to a maximum of 20% by weight of the formulation and preferably no more than 10%.

The above listing of polishing agents, and other listings of other constituents of the dentifrice composition to be given in the present specification are not intended to be exhaustive and therefore, for other materials of these types reference should be made to a standard handbook, such as Cosmetics: Science and Technology, by Sagarin, 2nd printing, 1963, published by Interscience Publishers, Inc.

Organic surface-active agents are used in the compositions of the present invention to assist in achieving thorough and complete dispersion of the instant compositions throughout the oral cavity and render the instant compositions more cosmetically acceptable. The organic surface-active material may be anionic, nonionic, ampholytic, or cationic in nature, and it is preferred to employ as the surface-active agent a detersive material which imparts to the composition detersive and foaming properties. Suitably such detergents are water-soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1,2-dihydroxy propane sulfonates, and the substantially saturated high aliphatic acyl amides of lower aliphatic amino carboxylic acid compounds, such as those having 12 to 16 carbon atoms in the fatty acid, or acyl radicals, and the like. Examples of the last mentioned amides are N-lauroyl sarcosine, and the sodium potassium and ethanolamine salts of N-lauroyl, N-myristoyl, or N-palmitoyl sarcosine which should be substantially free from soap or similar higher fatty acid material which tends to substantially reduce the effect of these compounds. The use of these sarcosinate compounds in the dentifrice compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Other particularly suitable surface-active materials include nonionic agents such as condensates of sorbitan monostearate with approximately 20 moles of ethylene oxide, condensates of ethylene oxide with propylene oxide, condensates of propylene glycol ("Pluronics"), and amphoteric agents such as quaternized imidazole derivatives which are available under the trademark "Miranol" such as Miranol $C_2M$.

Other suitable nonionic detergents are the condensation products of an α-olefin oxide containing 10 to 20 carbon atoms, a polyhydric alcohol containing 2 to 10 carbons and 2 to 6 hydroxyl groups and either ethylene oxide or a heteric mixture of ethylene oxide and propylene oxide. The resultant detergents are heteric polymers having a molecular weight in the range of 400 to about 1600 and containing 40% to 80% by weight of ethylene oxide, with an α-olefin oxide to polyhydric alcohol mole ratio in the range of bout 1:1 to 1:3. These detergents are manufactured using well-known polymerization techniques under conditions of high temperature and high pressure. The olefin oxide and polyhydric alcohol usually are added to the reactor prior to the addition of ethylene oxide. These nonionic detergents may be mixed with similar nonionic detergents as well as other types of nonionic detergents described herein.

There may also be employed olefin sulfonate detergents, typically long chain alkenyl sulfonates.

The α-olefin feedstock preferably contains olefins of 8–25 carbon atoms, most preferably 12–21 carbon atoms. The feedstock may contain minor amounts of other constituents, such as secondary or internal olefins, diolefins, cyclic olefins, aromatics, naphthalenes, and alkanes. Best results have been obtained when α-olefins (where $R_1$ is H) constitute a major proportion. A typical olefin feedstock contains in the range of about 12 to 21 carbon atoms in the molecule and yields olefin sulfonates having excellent detergency properties. Especially good foaming characteristics have been obtained by the use of a feedstock whose α-olefin content consists essentially of compounds of 15 to 18 carbon atoms.

The detergent material above produced, typically contains at least about 50% by weight of long-chain alkenyl sulfonate, up to about 33% by weight of hydroxy alkane sulfonate, and up to about 15% of impurities, such as long chain water-insoluble sultones, most of which impurities are characterized as being soluble in acetone.

The olefin sulfonate is generally employed in the form of its sodium salt. It is within the scope of this invention to use other water-soluble salts, for example, salts of other alkali metals such as potassium, salts of alkaline earth metals such as magnesium and calcium, triethanolamine salts and the like as well as mixtures of a salt such as a sodium salt with the free olefin sulfonic acid.

It is preferred to use from about 0.05 to 5% by weight and preferably about 0.5 to 5% of the foregoing surface-active materials in the instant oral preparations.

Various other compatible and suitable materials may be incorporated in the dentifrice formulations of this invention. Examples thereof are coloring or whitening agents or dyestuffs, preservatives, silicones, chlorophyll compounds, ammoniated materials such as urea, diammonium phosphate and mixtures thereof, and other constituents. These adjuvants are incorporated in the instant compositions in amounts which do not substantially adversely affect the properties and characteristics desired and are selected and used in proper amount depending upon the particular type of preparation involved.

Synthetic finely divided pyrogenic silica such as those sold under the trademark Cab-O-Sil M-5, Syloid 244, Syloid 266 and Aerosil D-200 may also be employed in amounts of about 1-5% by weight to promote thickening.

Antibacterial agents may also be employed in the oral preparation of the instant invention to provide a total content of such agents of up to about 5% by weight, preferably about 0.01 to 5.0%, most preferably about 0.05 to 1.0%. Typical antibacterial agents include:
$N^1$-(4-chlorobenzyl)-$N^5$-(2,4-dichlorobenzyl) biguanide;
p-chlorophenyl biguanide;
4-chlorobenzhydryl biguanido;
4-chlorobenzhydrylguanylurea;
N-3-lauroxypropyl-$N^5$-p-chlorobenzylbiguanide;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
1,6-di-p-chlorophenyl biguanidohexane;
1,6-bis(2-ethylhexyl biguanido) hexane;
5-amino-1,3-bis(2-ethylhexyl)-5-methylhexahydropyrimidine;
and their non-toxic acid addition salts.

The dentifrice may be prepared by suitably mixing the ingredients. For instance in making a toothpaste, the gelling agent, hydroxypropyl cellulose and a preservative such as dried benzoic acid, if employed, and sweetener, if used, is dispersed with the humectant propylene glycol. Dental abrasive agents, including the anhydrous zeolite, surface-active agent and flavor are then separately added and uniformly dispersed. The toothpaste is then thoroughly deaerated (e.g., in vacuo) and tubed. The addition and mixing of the ingredients is conducted in a low humidity environment and preferably under a vacuum of 20-30 inches and preferably 28-30 inches mercury.

Preferably the amount of water-soluble essential flavoring oil is above 0.5% and below 2%. Strongly flavored toothpastes contain above about 1% of such flavoring oil, e.g., about 1.2 to 1.5%.

The following Examples are given to illustrate this invention further. In this application all proportions are by weight unless indicated.

EXAMPLE I

Dental Cream

| Ingredients | % |
| --- | --- |
| Propylene glycol | 52.25 |
| Klucel GF | 2.00 |
| Benzoic acid | 0.15 |
| Sodium saccharin | 0.20 |
| TiO$_2$ | 0.40 |
| Sodium zeolite 4A (pH 10.35) | 41.00 |
| Pyrogenic silica (Syloid 244) | 1.00 |
| Sodium lauryl sulfate | 2.00 |
| Peppermint flavor | 1.00 |

The propylene glycol, Klucel, benzoic acid, saccharin and TiO$_2$ are heated to 180° F., mixed for 20 minutes and cooled. The zeolite powder, the Syloid, and the above gel mixture are mixed in a Hobart mixer until a uniform dispersion is obtained. The sodium lauryl sulfate and flavor are added to the mixture and thoroughly mixed until uniformly dispersed in the cream. Heat is generated during the mixing thereof, to a temperature of 120° F. This cream is deaerated and packaged in the conventional manner.

A 10% slurry of this cream has a pH of 8.9.

The resultant product exhibits thermal effects when used in the brushing of teeth, has a good consistency, but tends to flatten out on standing.

After standing at room temperature for 3 weeks, this cream exhibits no swelling in the tubes and generates heat in the mouth upon use, indicating stability of this cream.

EXAMPLE 2

Example 1 is repeated except that the pH of the zeolite 4A is adjusted to 9.59, a higher viscosity Klucel (MF) is used in order to thicken the cream and prevent the cream from flattening out, and another flavor is used.

This cream also generated heat during mixing (126° F.) and gave off an odor.

The resultant cream is very thick and generates heat when brushing the teeth therewith.

However, the cream is not as stable as the product of Example 1, as evidenced by the minor swelling in the tubes after 2 weeks, although it retains its original thickness. Less heat is generated when brushing.

EXAMPLE 3

Example 2 is repeated except that the Klucel MF is reduced to 1% and the propylene glycol is increased to 53.25%.

The resultant cream is on the thick side. After 2 weeks, this cream swells in the dental tubes, becomes thick and gummy with air pockets and oozes.

10 gms of this cream + 5.2 gms water effects a temperature rise to 44° C. from room temperature.

Despite the cosmetically unacceptable consistency and stability of this cream, it nevertheless is self-heating.

EXAMPLE 4

| Ingredients | % |
| --- | --- |
| Propylene Glycol | 27.82 |
| Klucel GF | 1.48 |
| Benzoic acid | 0.185 |
| Sodium saccharin | 0.148 |

| Ingredients | % |
| --- | --- |
| TiO₂ | 0.296 |
| Zeolite 4A | 30.370 |
| Syloid 244 | 0.741 |
| Zeo 49[1] (abrasive) | 10.815 |
| Sodium lauryl sulfate | 1.48 |
| Flavor | 0.741 |
| Additional Propylene glycol | 25.93 |

[1]Trademark for an amorphous sodium alumino-silicate containing about 89-91% silica, about 0.81-1.2% alumina, about 1.3-0.9% sodium oxide and about 10% water.

The Klucel is added to 27.82% propylene glycol and heated to 130°-140° F., followed by the addition of benzoic acid, saccharine and TiO₂ and the mixture is agitated for 20 minutes. The zeolite, Syloid, Zeo 49 and flavor are added and mixed, yielding a thick cream. 25.93% additional propylene glycol is added but the cream is still on the thick side. The propylene glycol has a disagreeable odor when heated.

After 2 weeks, this cream exhibits some swelling in the tubes and still has a slightly thick consistency.

EXAMPLE 5

Example 1 is repeated except that the saccharin is omitted and the propylene glycol content is increased to 52.45%.

1 gm of cream+0.5 gm distilled water effected an elevation in the temperature from 26° C. to 36° C.

5 gms cream+2.5 cms H₂O caused the temperature to rise from 26° C. to 36° C. in 30 seconds, to 40° C. in 40 seconds, to 41° C. in 60 seconds. The temperature dropped to 38° C. in 2 minutes and to 35° C. in 3-4 minutes.

EXAMPLE 6

| Ingredients | Amount (grams) |
| --- | --- |
| Zeolite 4A | 82 |
| Propylene glycol | 107 |
| Benzoic acid | 0.3 |
| TiO₂ | 0.8 |
| Syloid 244 | 2.0 |
| Sodium lauryl sulfate | 4.0 |
| Flavor | 2.0 |
| Klucel MF | 4.0 |

41 gms of the zeolite is slurried with the propylene glycol at room temperature of 72° F. Each of the ingredients is separately added without mixing in the order listed, ending with the addition of the remainder of the 41 gms of zeolite. No heat is evolved upon the addition of any of the ingredients.

The cream starts to thicken, is deaerated without mixing and tubed. Although this cream is stiff and hard to squeeze from the tubes, brushing the teeth therewith evolves more heat than with the creams prepared in the Hobart mixer of the previous examples.

EXAMPLE 7

The dental cream of Example 1 is compounded under vacuum in accordance with the following procedure.

The Klucel, benzoic acid, and saccharin are added and dispersed in the propylene glycol and heated to 120°-140° F. with agitation for about 20 minutes, using a hot water bath. The heat is turned off at 115° F., but the temperature rises to 120° F. and after 20 minutes to 140° F. The mix starts to gel after 10 minutes of mixing. The mix is cooled to 100°-110° F. and the gel starts to thicken upon cooling.

The abrasive system TiO₂, zeolite, and Syloid are placed into a Ross mixer equipped with a vacuum. The gel mixture is added thereto and the vacuum is raised to 20-25 inches. The mixture is blended and agitated for 35 minutes. The vacuum is broken and the sodium lauryl sulfate and flavor are added. The mixture is subjected to a vacuum of 28-29 inches, blended and agitated for about 15 minutes. The mixing is terminated and the vacuum is allowed to evacuate for about 5-10 minutes. The cream is filled into tubes.

5 gms cream+2.5 gms H₂O effects a rise from an initial temperature of 26° C. to 41° C. in 1 minute, which drops to 39° C. in 2 minutes, 38° C. in 3 minutes, and 35°-36° C. in 4 minutes. The heat release is sustained for the total brushing action.

Aging the dental tube at 110°-120° F. showed no swelling after 3 weeks.

This example clearly shows that the use of a vacuum during the compounding of the cream effects a more stable product.

EXAMPLE 8

Example 7 is repeated except that 15% glycerin replaces 15% of the propylene glycol. The vacuum utilized for the blending of the gel with the abrasives is 25-28 inches.

After aging for 1 week, the tubes showed a slight bulge.

5 gms cream+2.5 gms H₂O causes the temperature to rise from 25°-26° C. to 30° C. in 15 seconds, 35° C. in 30 seconds, 40° C. in 45 seconds, 42° C. in 60 seconds, 42°-43° C. in 90 seconds, 42° C. in 120 seconds, 38°-39° C. in 180 seconds.

However, then substitution of 32% glycerine for 32% of the propylene glycol in the above formulation does not produce a gel with the Klucel, indicating that glycerine is not compatible with Klucel.

Thus, it is apparant that although 15% glycerine in the propylene glycol humectant system renders it compatible with the hydroxypropyl cellulose gel, it nevertheless adversely affects the stability of the dental cream.

EXAMPLE 9

A slurry of zeolite in propylene glycol is made containing 48.387% zeolite and 51.613% propylene glycol.

| Ingredient | % |
| --- | --- |
| Propylene glycol | 20.250 |
| Klucel GF | 2.0 |
| Benzoic acid | 0.15 |
| Sodium saccharin | 0.2 |
| TiO₂ | 0.4 |
| Zeolite powder | 11.0 |
| Syloid 244 | 1.0 |
| Zeolite slurry | 62.0 |
| Sodium lauryl sulfate | 2.0 |
| Flavor | 1.0 |

The Klucel and propylene glycol gel are made as in the previous examples.

The powdered abrasives TiO₂, zeolite and Syloid are added to the gel. 62% of the zeolite slurry is added on top of the dried powder, but is hard to blend into the dry powder. The sodium lauryl sulfate and the flavor are added and mixed well. The batch is deaerated for 10–12 minutes. The cream appears to be thicker than normal.

1 gm of this hot dental cream+0.5 gm $H_2O$ elevated the temperature of the water from 25° C. to 36° C.

5 gms of this hot dental cream+2.5 gms $H_2O$ causes the temperature of the water to rise from 25° C. to 36° C. in 30 seconds, to 41° C. in 40 seconds, to 42° C. in 60 seconds and falls to 40° C. in 120 seconds.

5 gms of the zeolite and propylene glycol slurry+2.5 gms $H_2O$ causes the temperature to rise to 50° C. in 15 seconds.

Aging at 110°–120° F. results in a slight swelling in the tubes.

EXAMPLE 10

Example 7 is repeated except that the vacuum is maintained at 28–29 inches during the blending and mixing of the ingredients.

The resultant cream is smooth, exhibits no swelling in the tubes and releases heat when brushing the teeth even after standing at room temperature for 7 months.

This illustrates the exceptional stability obtained with the use of a vacuum of 28–29 inches during the compounding of the dental cream.

EXAMPLE 11

Example 10 is repeated except that the zeolite content is reduced to 31.0%, 10.4% Zeo 49 is added and the Klucel content is reduced to 1.6%.

The tubes containing the dental cream exhibits no swelling after aging for 7 months at room temperature. The cream is smooth and releases heat when brushing the teeth.

EXAMPLE 12

Example 10 is repeated except that 0.2% of GF Klucel is replaced with MF Klucel.

After aging for 7 months at room temperature, the resultant cream is smooth, is heat releasing in the mouth and the tubes exhibit no swelling.

Examples 10–12 wherein a vacuum of 28–29 inches is utilized represents the preferred method of producing a stable, smooth, self-heating dental cream possessing a good shelf-life.

Other examples may be compounded wherein the sodium zeolite is replaced in part or in total by other metal zeolites such as copper, zinc, other alkali metals, magnesium, calcium and other alkaline earth metals. Similarly, in lieu of the 4A zeolite, the 3A or 5A zeolites may be utilized. The major physical difference between the 5A, the 4A and the 3A zeolites is in the critical pore diameter, which is 5, 4 and 3 angstroms respectively and can therefore absorb molecules with critical diameters up to 5, 4 and 3 respectively.

Still other examples may be compounded wherein the flavor or flavors are changed to spearmint, eucalyptus, anethole, menthol, carvone, lemon, orange, etc., and the proportions varied over a 0.5 to 5% range, and preferably 0.5 to 2% for best taste effects.

Similarly, examples may be formulated wherein other surfactants such as sodium-N-lauroylsarcosinate and any of the other listed surfactants or mixtures thereof are substituted for the sodium lauryl sulfate as well as other gelling agents, humectants or mixtures thereof.

The pH of the dentifrices is generally within the range of about 7 to 9.5.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A stable anhydrous self-contained heat releasing dentifrice which generates heat in the mouth consisting of a finely divided anhydrous synthetic zeolite having an appreciable heat of hydration and capable of being reversibly dehydrated as the sole or major polishing agent in amounts of about 20 to 50% by weight, about 0.1 to 5% by weight of at least one flavoring agent, and about 20 to 75% of an anhydrous liquid vehicle, consisting essentially of propylene glycol gelled with a finely divided solid hydroxy-propyl cellulose polymer having a molecular weight of 60,000–1,000,000, said dentifrice being prepared in a substantially anhydrous environment.

2. A dentifrice according to claim 1, wherein the synthetic zeolite is a crystalline metal alumino silicate, said metal being selected from the group consisting of an alkali metal, alkaline earth metal, zinc, copper and mixtures thereof.

3. A dentifrice in accordance with claim 1, wherein the gelling agent constitutes about 1–5% by weight of the total formulation, and the propylene glycol constitutes 35–60% by weight thereof.

4. A dentifrice in accordance with claim 1, which additionally contains about 0.5 to 5% of a surface-active agent.

5. A dentifrice according to claim 4, wherein the surface-active agent is anionic.

6. A dentifrice in accordance with claim 5, which also contains a sweetening agent and wherein the flavoring agent is a flavoring oil in an amount of about 0.5 to 2% by weight.

7. A dentifrice in accordance with claim 1, which contains up to about 20% of an additional dentally acceptable, water-insoluble, anhydrous finely divided polishing agent.

8. A dentifrice in accordance with claim 1, wherein the gelling agent is hydroxypropyl cellulose polymer having a molecular weight of about 300,000.

9. A dentifrice in accordance with claim 7, wherein said additional polishing agent is an amorphous alkali metal or alkaline earth metal alumino-silicate containing at least 70% silica, up to about 10% alumina and up to about 10% sodium oxide.

10. A dentifrice in accordance with claim 3, wherein the anhydrous environment constitutes a vacuum of at least about 20 inches and up to 30 inches mercury.

* * * * *